(12) United States Patent
Bush et al.

(10) Patent No.: US 8,775,961 B2
(45) Date of Patent: *Jul. 8, 2014

(54) METHODS, SYSTEMS AND COMPUTER READABLE MEDIA FOR MODIFYING PARAMETERS OF A CONFIGURATION FILE

(71) Applicant: Roche Diagnostics Operations, Inc., Indianapolis, IN (US)

(72) Inventors: Jason M. Bush, Fishers, IN (US); David B. Markisohn, Indianapolis, IN (US); Kristin Westerfield, Fortville, IN (US); Laura Wilkerson, Indianapolis, IN (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/899,899

(22) Filed: May 22, 2013

(65) Prior Publication Data

US 2013/0254697 A1    Sep. 26, 2013

Related U.S. Application Data

(63) Continuation of application No. 12/641,628, filed on Dec. 18, 2009, now Pat. No. 8,495,515.

(51) Int. Cl.
*G06F 3/0484* (2013.01)
*G06F 3/00* (2006.01)
*G06F 19/00* (2011.01)

(52) U.S. Cl.
CPC ........ *G06F 3/04847* (2013.01); *G06F 19/3406* (2013.01); *G06F 19/3456* (2013.01)
USPC .......................................... 715/771; 715/866

(58) Field of Classification Search
USPC .................... 715/771, 866; 600/365; 604/892
See application file for complete search history.

(56) References Cited

U.S. PATENT DOCUMENTS

| 5,620,608 | A | 4/1997 | Rosa et al. |
| 6,810,290 | B2 * | 10/2004 | Lebel et al. ..................... 607/60 |
| 8,452,953 | B2 * | 5/2013 | Buck et al. ..................... 713/100 |
| 8,495,515 | B2 * | 7/2013 | Bush et al. ..................... 715/771 |
| 2002/0083003 | A1 | 6/2002 | Halliday et al. |
| 2003/0060765 | A1 | 3/2003 | Campbell et al. |

(Continued)

FOREIGN PATENT DOCUMENTS

WO    03022327 A2    3/2003

OTHER PUBLICATIONS

International Search Report and Written Opinion regarding PCT/US2010/060433 dated Mar. 3, 2011.

(Continued)

*Primary Examiner* — Steven Sax
*Assistant Examiner* — Wilson Varga
(74) *Attorney, Agent, or Firm* — Dinsmore & Shohl LLP

(57) ABSTRACT

Disclosed is a method of configuring a medical device through utilization of a computing device that includes a user interface, a processor and memory. The method includes the steps of determining whether a configuration file contains a focal modified parameter, displaying the focal modified parameter, prompting a manual re-entry of the displayed focal modified parameter, receiving through the user interface the manual re-entry of the displayed focal modified parameter, and utilizing the processor to automatically determine whether the manual re-entry of the displayed focal modified parameter matches the displayed focal modified parameter.

18 Claims, 16 Drawing Sheets

(56) References Cited

U.S. PATENT DOCUMENTS

| | | |
|---|---|---|
| 2003/0163789 A1 | 8/2003 | Blomquist |
| 2004/0148513 A1* | 7/2004 | Scott et al. .................. 713/200 |
| 2005/0022274 A1 | 1/2005 | Campbell et al. |
| 2006/0009734 A1 | 1/2006 | Martin |
| 2007/0106135 A1 | 5/2007 | Sloan et al. |
| 2007/0112298 A1 | 5/2007 | Mueller, Jr. et al. |
| 2007/0118405 A1 | 5/2007 | Campbell et al. |
| 2008/0091175 A1 | 4/2008 | Frikart et al. |
| 2008/0126968 A1 | 5/2008 | West et al. |
| 2008/0319384 A1 | 12/2008 | Yodfat et al. |
| 2009/0005726 A1 | 1/2009 | Jones et al. |
| 2009/0043290 A1* | 2/2009 | Villegas et al. ............ 604/891.1 |
| 2009/0183147 A1* | 7/2009 | Davis et al. .................... 717/168 |
| 2010/0077198 A1* | 3/2010 | Buck et al. .................... 713/100 |

OTHER PUBLICATIONS

Office Action pertaining to U.S. Appl. No. 12/641,628 dated Apr. 13, 2012.

Office Action pertaining to U.S. Appl. No. 12/641,628 dated Aug. 30, 2012.

Notice of Allowance pertaining to U.S. Appl. No. 12/641,628 dated Apr. 2, 2013.

* cited by examiner

METHODS, SYSTEMS AND COMPUTER READABLE MEDIA FOR MODIFYING PARAMETERS OF A CONFIGURATION FILE

CROSS-REFERENCE TO RELATED APPLICATIONS

This application is a continuation of U.S. application Ser. No. 12/641,628, filed Dec. 18, 2009.

TECHNICAL FIELD

The invention relates to methods, systems and computer readable media for modifying parameters of a configuration file that is written to a medical device.

BACKGROUND

Diabetes is a disease in which the body does not produce or properly use insulin. To effectively manage the disease, diabetics must closely monitor and manage their blood glucose levels through exercise, diet and medication. In some situations, diabetics may also rely on insulin delivery to control the effects of the disease. Traditionally, insulin was injected with a syringe multiple times during the day. However, developments in technology currently allow for the delivery of insulin from a reservoir via a catheter with a percutaneous needle or cannula placed in the subcutaneous tissue. A programmable insulin pump controls the delivery of insulin according to a individualized configuration file (i.e., a set of delivery parameters). For example, a small amount of insulin, or a basal rate, may be continually delivered to a user. The basal rate keeps the user's blood glucose levels in the desired range between meals and during sleep. When food is eaten, the user may further control the pump to deliver an additional bolus (i.e., set dose) of insulin to counteract the effect that the ingested food has on the user's blood glucose levels.

However, errors in setting or modifying the pump configuration file parameters (e.g., too large or small of a basal rate and/or bolus amount, etc.) may lead to serious health consequences for the user. Accordingly, error-reducing methods, systems and computer readable media utilized in the setting and/or modification of the parameters of a pump configuration file (or a configuration file for any other medical device) are of continued interest.

SUMMARY

One embodiment of a method of configuring a medical device through utilization of a computing device that includes a user interface, a processor and memory, includes the steps of: receiving in memory a configuration file with one or more modified parameters; establishing communication between the medical device and the computing device; utilizing the processor to automatically read the configuration file from memory, determine whether the configuration file contains modified parameters that are focal, display the modified parameters on the user interface, and prompt a confirmation of the displayed modified parameters; receiving through the user interface the confirmation of the displayed modified parameters; utilizing the processor to automatically display a determined focal modified parameter on the user interface, and prompt a manual re-entry of the displayed focal modified parameter; receiving through the user interface the manual re-entry of the displayed focal modified parameter; utilizing the processor to automatically determine whether the manual re-entry of the displayed focal modified parameter matches the displayed focal modified parameter, and designate the displayed focal modified parameter as valid if the manual re-entry of the displayed focal modified parameter matches the displayed focal modified parameter, otherwise prompt for another manual re-entry of the displayed focal modified parameter or a change to the configuration file; and utilizing the processor to automatically write the configuration file to the medical device once every determined focal modified parameter has been designated valid.

One embodiment of a computer readable medium tangibly embodying a program of instructions executable by a computing device to perform method steps includes reading a configuration file with one or more modified parameters from memory, determining whether the configuration file contains modified parameters that are focal, displaying the modified parameters, prompting an operator to confirm the displayed modified parameters, receiving a confirmation of the displayed modified parameters, displaying a determined focal modified parameter, prompting a manual re-entry of the displayed focal modified parameter, receiving the manual re-entry of the displayed focal modified parameter, determining whether the manual re-entry of the displayed focal modified parameter matches the displayed focal modified parameter, designating the displayed focal modified parameter as valid if the manual re-entry of the displayed focal modified parameter matches the displayed focal modified parameter, otherwise prompting for another manual re-entry of the displayed focal modified parameter or a change to the configuration file, and writing the configuration file to a medical device once every determined focal modified parameter has been designated valid.

One embodiment of a system for configuring a medical device includes a computing device that includes a user interface, a processor and memory, and software stored in memory for execution by the computing device, the software facilitating a workflow including the steps of reading a configuration file with one or more modified parameters from memory, determining whether the configuration file contains modified parameters that are focal, displaying the modified parameters, prompting an operator to confirm the displayed modified parameters, receiving a confirmation of the displayed modified parameters, displaying a determined focal modified parameter, prompting a manual re-entry of the displayed focal modified parameter, receiving the manual re-entry of the displayed focal modified parameter, determining whether the manual re-entry of the displayed focal modified parameter matches the displayed focal modified parameter, designating the displayed focal modified parameter as valid if the manual re-entry of the displayed focal modified parameter matches the displayed focal modified parameter, otherwise prompting for another manual re-entry of the displayed focal modified parameter or a change to the configuration file, and writing the configuration file to a medical device once every determined focal modified parameter has been designated valid.

BRIEF DESCRIPTION OF THE DRAWINGS

Aspects of the teachings herein will be more apparent and better understood by reference to the following description of embodiments taken in conjunction with the accompanying drawings, wherein.

DETAILED DESCRIPTION

Figure 1:
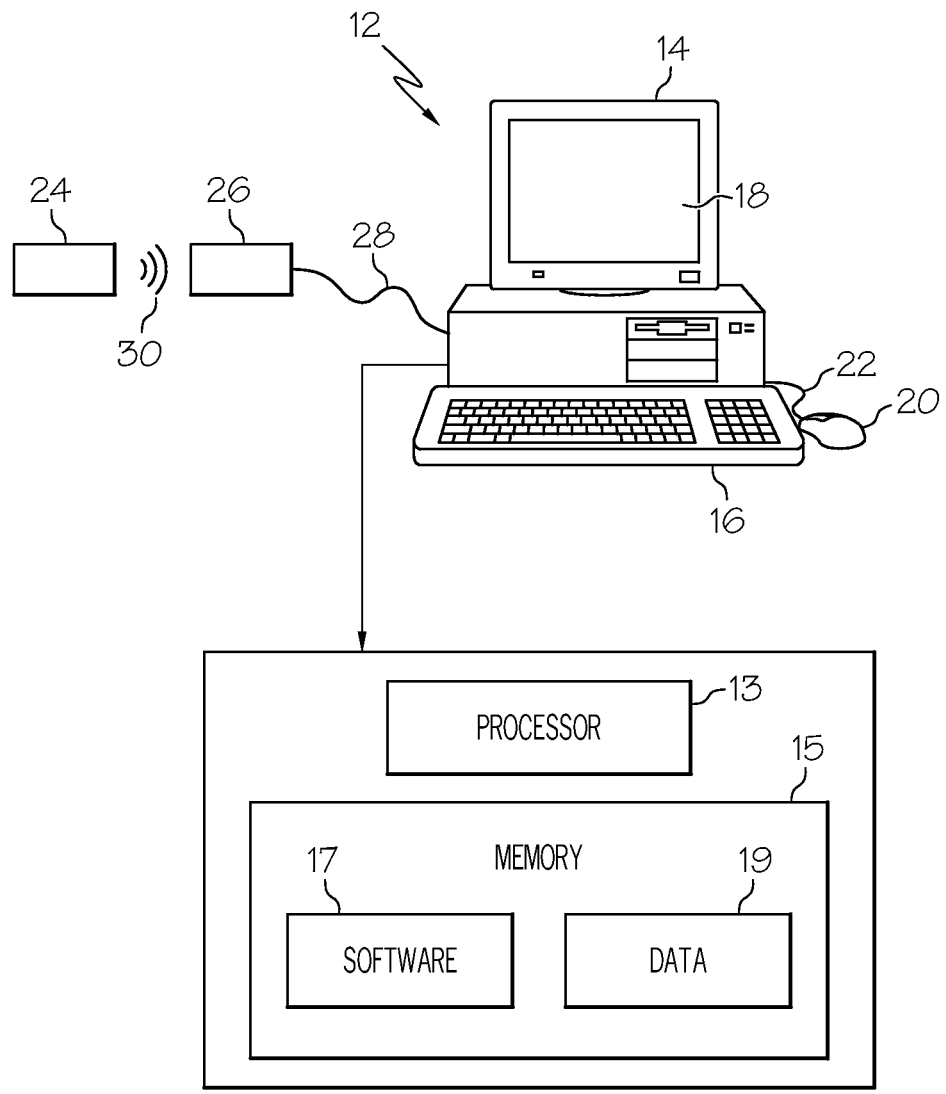
FIG. 1 is a conceptual diagram of a computing device in communication with a medical device.

Embodiments of methods, systems and computer readable media described herein relate to setting and/or modifying focal parameters of a configuration file of a medical device. The embodiments of the teachings described below are not intended to be exhaustive or to limit the teachings to the precise forms disclosed in the following detailed description. Rather, the embodiments are chosen and described so that others skilled in the art may appreciate and understand the principles and practices of the present teachings.

Accordingly, it should be understood that although the concepts below are described as relating to insulin pumps and insulin pump configuration software, such as the ACCU-CHEK® Insulin Pump Configuration Software provided by Roche Diagnostics Corporation, the concepts also relate to diabetes management software systems for tracking and analyzing health data, such as, for example, the ACCU-CHEK® 360° product provided by Roche Diagnostics Corporation, as well as any other medical device or medical device software that incorporates a configuration file (e.g., basic blood-glucose meters, advanced blood-glucose meters, etc.). The concepts also relate to hub devices and pass-through devices that communicate with and/or control one or more medical devices. Moreover, the concepts described herein may also have applicability to apparatuses, methods, systems, and software in fields that are unrelated to healthcare. Furthermore, it should be understood that references in this patent application to devices, pumps, meters, monitors, or related items are intended to encompass any currently existing or later developed apparatus that includes some or all of the features attributed to the detailed apparatus, including but not limited to, the ACCU-CHEK® Active, ACCU-CHEK® Aviva, ACCU-CHEK® Compact, ACCU-CHEK® Compact Plus, ACCU-CHEK® Integra, ACCU-CHEK® Go, ACCU-CHEK® Performa, ACCU-CHEK® Spirit, ACCU-CHEK® D-Tron Plus, and ACCU-CHEK® Voicemate Plus, all provided by Roche Diagnostics Corporation or divisions thereof.

An insulin pump (e.g., ACCU-CHEK® Spirit) is a fluid infusion device for delivering insulin to people who suffer from diabetes. The pump, which is worn by the user and eliminates the need for multiple daily insulin injections, closely imitates a normally functioning pancreas by releasing hundreds of small doses of insulin each day into the body through an infusion set to regulate blood glucose levels. The rate of delivery of these small doses (i.e., the basal rate) varies from user to user. Indeed, even for a particular user, the basal rate may vary throughout the day, and depends upon a variety of factors such as the user's internal clock, metabolism, physical health, and level of stress and exercise. Insulin pumps may also deliver (either automatically or when activated by the user) bolus doses of insulin (in addition to the basal rate) before meals or snacks to compensate for caloric intake.

As the amount and rate of insulin delivery (both basal and bolus) must be tailored to the individual needs of the user, modern pumps are programmable. Some pumps are capable of communicating with a separate computing device, and are compatible with software applications that may be executed on the computing device. The software permits an operator, such as the user or a health care provider, to customize the settings of the various parameters that affect the operation of the pump. These parameters are encompassed in a configuration file that is executed by the pump, and may include hourly basal rates, maximum hourly basal rates, maximum daily basal rates, bolus dose settings, communication settings, battery settings, and many others. For example, using programming software on a computing device, a user may upload a configuration file from their pump, modify the settings for certain parameters to change the operation of the pump, and save the modified configuration file to the pump. Alternatively, a health care provider responsible for programming the pumps of multiple patients may select an initial configuration file stored on a pump or computing device as a starting point for programming the patients' pumps. Many of the parameter settings of the initial configuration file (e.g., battery type, language, etc.) may be suitable for all of the pumps to be programmed. Other settings (e.g., total daily basal rates, bolus dose settings, etc.) may be unique to each patient's pump. After the health care provider selects the initial configuration file, he or she may change only the settings needed to customize the pump's operation for an individual patient, then save the customized configuration file to that patient's pump without having to define a setting for every pump parameter.

Referring to the figures, FIG. 1 depicts an exemplary embodiment of a computing device 12, some or all of the components of which may be used in conjunction with the teachings of the present disclosure. Computing device 12, shown here in the form of a computer, generally includes a user interface 14 (including a video screen or monitor having screen 18 and a keyboard 16), a processor 13 and memory 15, which may contain and/or access the software 17 of the present disclosure and data 19 as is further described herein. Computing device 12 may also incorporate a pointing device or mouse 20 connected to it by cable 22 (or wirelessly). In addition, while mouse 20 and keyboard 16 are illustrated, computing device 12 may also include any other input device such as a touchpad, joystick, touch screen, trackball, etc.

While described and depicted herein with specific reference to a computer, certain concepts of the present disclosure may be utilized in conjunction with any type of computing device capable of operating medical device programming software, such as, for example, a medical website, a hub device, a stand-alone device (e.g., a blood-glucose meter, a personal digital assistant), a pass-through device (e.g., a blood-glucose meter with pass-through capability) and/or a computing device incorporated on or within the medical device. Further, any type of computing device may be used in conjunction with a hub device and/or a pass-through device in the communication with and/or control of one or more medical devices. For example, in one embodiment, the computing device may be a computer, medical website and/or stand-alone device that is utilized to communicate with a hub device, that in turn, controls one or more configurable medical devices. In another embodiment, the computing device may be a computer, medical website and/or stand-alone device that is utilized to communicate with a blood-glucose meter with pass-through capability, that in turn, controls a configurable medical device. In another embodiment, the computing device is the hub device that controls one or more configurable medical devices.

Memory 15 of computing device 12 may include a variety of computer-readable media. Computer-readable media can be any available media that can be accessed by computing device 12 and includes both volatile and non-volatile media, and removable and non-removable media. By way of example, and not limitation, computer-readable media may comprise computer storage media and communication media. Storage media includes, but is not limited to, RAM, ROM, EEPROM, flash memory or other memory technology, CD-ROM, Digital Versatile Disk (DVD) or other optical disk storage, magnetic cassettes, magnetic tape, magnetic disk storage or other magnetic storage devices, or any other medium which can be used to store computer-readable instructions, software, data structures, program modules and other data and which can be accessed by computing device 12. Computer-readable media may be accessed directly or through a network such as the Internet.

Still referring to FIG. 1, computing device 12 is configured to provide information to, and receive information from, a medical device 24 (e.g., an insulin pump or other configurable device). Again, while an insulin pump is specifically described herein as medical device 24, it should be understood that the teachings of the present disclosure may also apply to other medical devices that utilize configuration files, such as, for example, "smart" insulin pens or other such devices known or hereafter developed. Computing device 12 is shown coupled to communication media or dongle 26, in this case a modulated signal transceiver, accessible to computing device 12 by means of cable 28, and configured to transmit and receive modulated signal 30 to establish logical communication with medical device 24. In another exemplary embodiment, computing device 12 and medical device 24 may include ports configured to establish a physical connection. By way of example, and not limitation, dongle 26 may include wired media such as a wired network or direct wired connection, and wireless media such as acoustic, RF, infrared, Bluetooth® and other wireless media. More specifically, dongle 26 as depicted includes an infrared port for communication with a similar infrared port for medical device 24.

Figure 2:
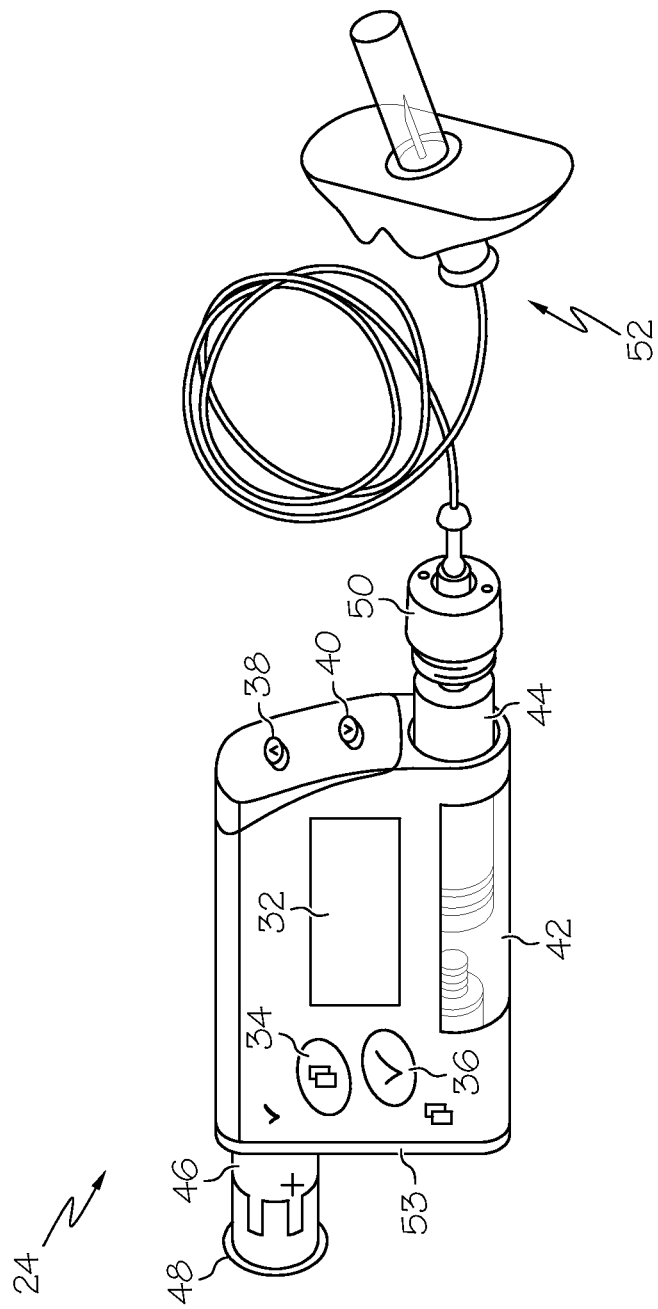
FIG. 2 is a perspective view of an insulin pump.

Referring to FIG. 2, medical device 24 is depicted as an insulin pump that includes a display 32 for displaying information to an operator or user, a menu button 34 for navigating though the various functions provided by medical device 24, a check button 36 for selecting options, an up key 38 and down key 40 for scrolling through options and controlling certain insulin delivery functions, a cartridge receptacle 42 for storing an insulin cartridge 44, a battery 46 (shown partially inserted), a battery cap 48 (shown unsecured to medical device 24), an adapter 50 for physically coupling cartridge 44 to an infusion set 52, and a communication port 53 for sending information to, or receiving information from, computing device 12 through dongle 26.

Figure 3:
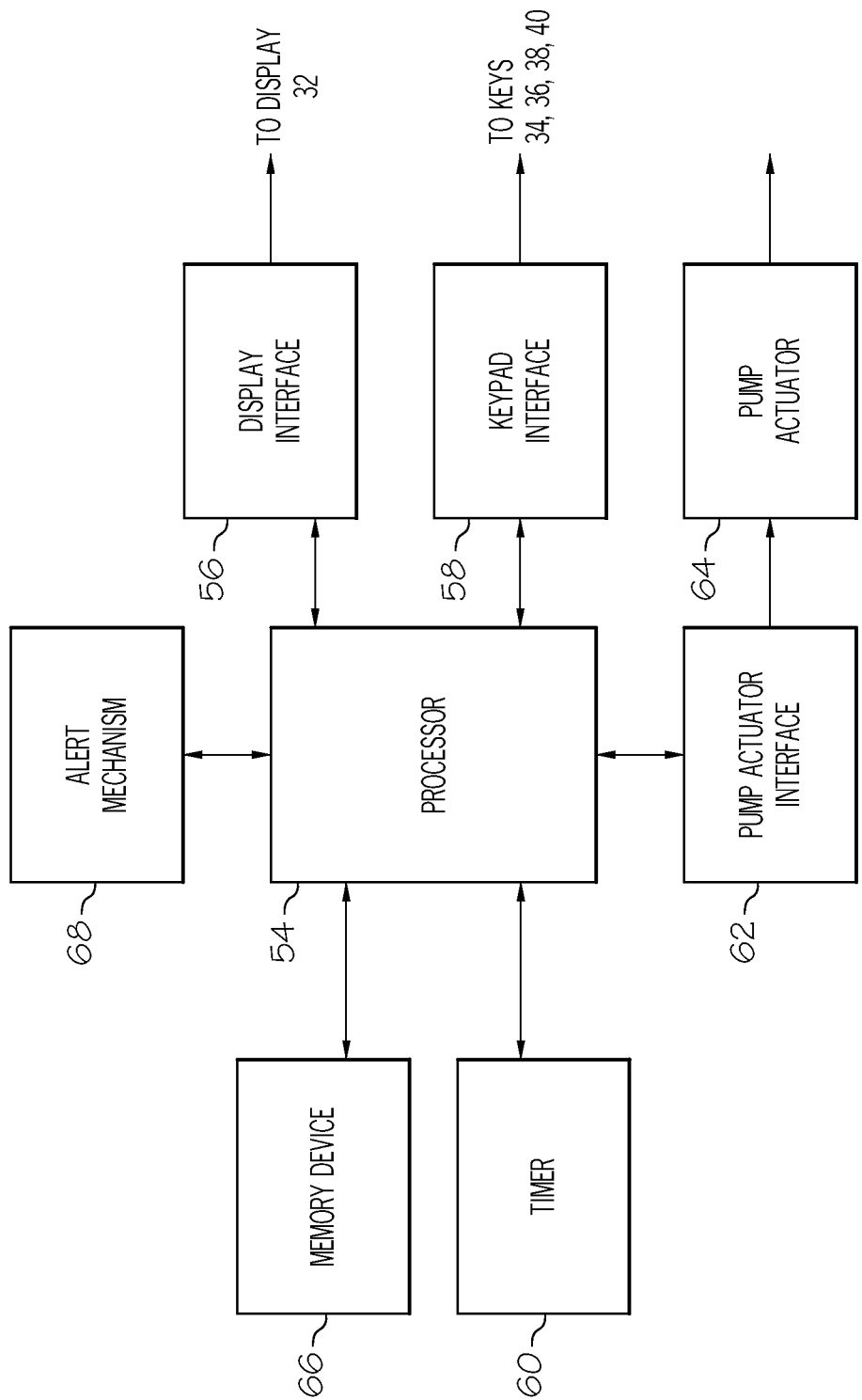
FIG. 3 is a block diagram of the internal components of the insulin pump of FIG. 2.

FIG. 3 provides a block diagram representation of internal components of medical device 24. As shown, medical device 24 may include a processor 54 coupled to a display interface 56, which is coupled to display 32. Processor 54 may also be coupled to a keypad interface 58 which is coupled to keys 34, 36, 38, 40, and a pump actuator interface 62 which is coupled to an actuator 64 suitable for delivering insulin doses (medical infusion pumps other than insulin pumps will deliver doses of other medicament). Processor 54 is further coupled to a memory device 66 that stores application programs and data, including the configuration files described herein. Memory device 66 may be constructed of any combination of volatile and/or nonvolatile memory suitable for a particular embodiment. Processor 54 may also be coupled to an alert mechanism 68, that, in various embodiments is a buzzer, a vibrator, a light emitting diode, or the like, suitable for providing audible, tactile, or visual alerts to an insulin pump user. Finally, processor 54 may be coupled to a timer 60, which is capable of maintaining a current time, including time of day and day of the week.

In the context of the above-detailed computing device 12 and medical device 24, embodiments of the methods, systems and computer readable media of the present teachings relate to the utilization of the computing device in adjusting the parameters, in particular the focal parameters, of a configuration file utilized by the medical device. The term "focal parameters" may be defined broadly or narrowly, depending on the desired application of medical device 24. For example, in an application where medical device 24 is an insulin pump, the focal parameters may include parameters relating to insulin dosage rates, such as, for example, the parameters of total daily basal amount and bolus doses (e.g., maximum dose and standard increment). However, the focal parameters may include any other desired parameter of a configuration file, and are therefore not limited to the above-detailed exemplary parameters. Further, in embodiments of the methods, systems and computer readable media that employ medical device 24 that is not an insulin pump, focal parameters may include any parameter(s) designated as focal.

Figure 4:
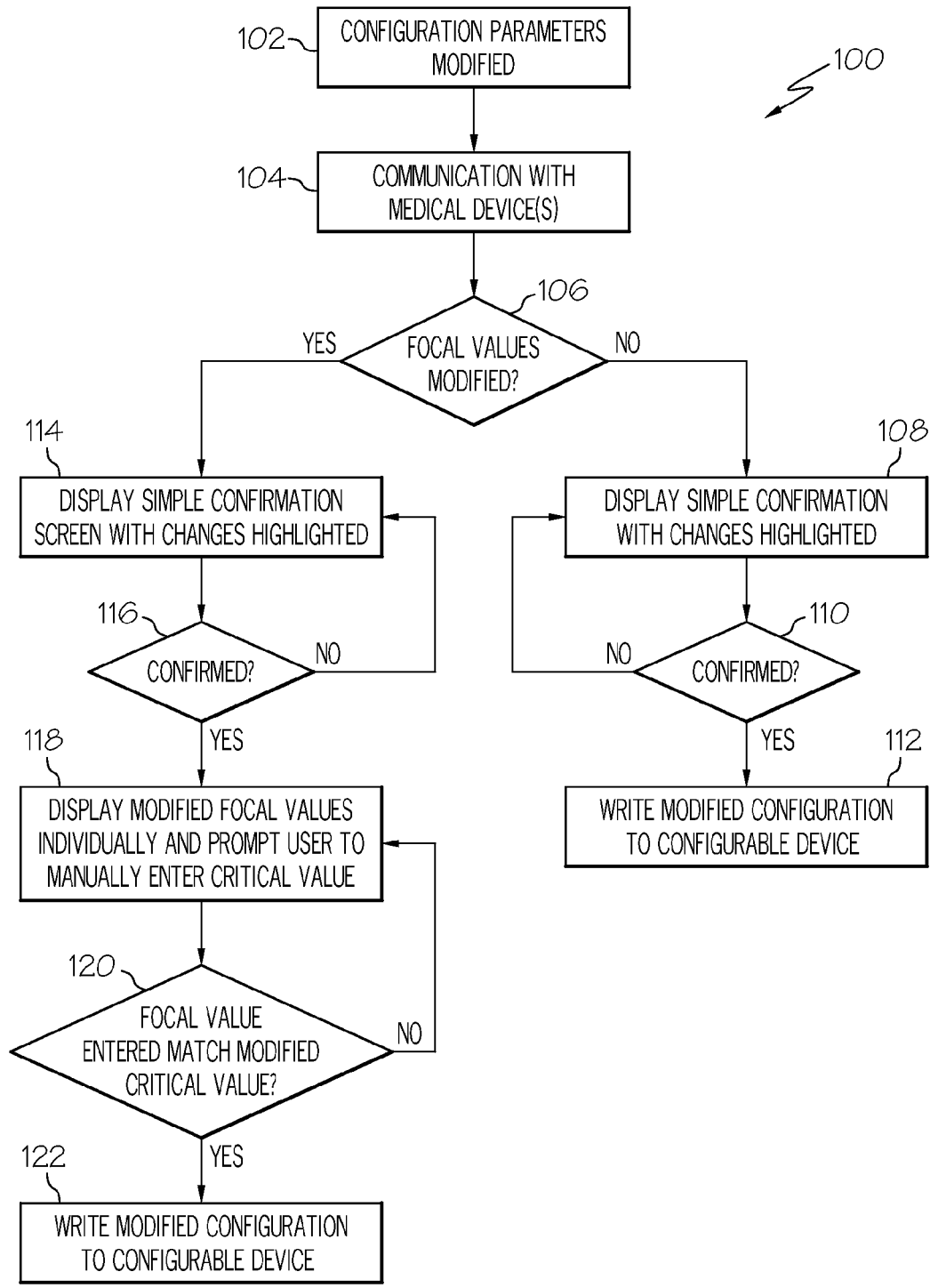
FIG. 4 is a block diagram of an embodiment of a method and/or workflow of modifying configuration file parameters.

Referring to FIG. 4, a block diagram representation of an embodiment of a method or workflow (executable by computing device 12) that modifies parameters of a configuration file of a medical device is illustrated. The depicted embodiment of method and/or workflow 100 includes a step 102 for the initial setting, adjusting or modifying of one or more parameters of a configuration file. Any parameter(s) that is encompassed in a configuration file may be initially set or modified in this step. In embodiments where the configuration file relates to an insulin pump, examples of such parameters may include hourly basal rates, maximum hourly basal rates, maximum daily basal rates, bolus dose settings, communication settings, battery settings, language settings and many others. After one or more parameters of the configuration file are set or modified, the configuration file may then be received in memory 15 of computing device 12.

Another step 104 provides that communication is established between medical device 24 and computing device 12. As detailed above, the communication may be established through wires or wirelessly, through dongle 26 or otherwise. However, in embodiments that may have computing device 12 incorporated within medical device 24, communication between the two may have already been established, on a temporary or permanent basis. In other embodiments, the communication between medical device 24 and computing device 12 may further utilize a hub device or a pass-through device. In embodiments that include a hub device, computing device 12 communicates with the hub device and the hub device sends the communication to one or more medical devices 24. In embodiments that include a pass-through device, computing equipment 12 communicates with the pass-through device, and the pass-through device then passes the communication along to one or more medical devices 24. Also, as detailed above, computing device 12 may comprise the hub device.

In some embodiments of method and/or workflow 100, step 102 may involve a user uploading a configuration file from the user's medical device and modifying the settings for certain parameters. In such an embodiment, communication would have to have already been established between medical device 24 and computing device 12 to allow for the uploading of the configuration file from the medical device to the computing device. Accordingly, in such embodiments, step 104 may precede step 102. However, in other embodiments, step 102 may involve a health care provider selecting an initial configuration file stored on computing device 12 as a starting point. In such embodiments, steps 102 and 104 may be ordered as illustrated in FIG. 4. Therefore, the ordering of steps 102 and 104, as well as the ordering of any other steps in method and/or workflow 100 described herein, should not be restricted to the illustrated arrangement of the embodiment of FIG. 4.

Once the parameters of the configuration file are set and/or modified, and communication is established between computing device 12 and the medical device 24, step 106 may be automatically executed by processor 13 of the computing device. In this step, processor 13 utilizes logic to determine if any of the one or more modified parameters of the configuration file are focal. As detailed above, focal parameters may be defined on an application-by-application basis. In one embodiment where medical device 24 is an insulin pump, non-limiting examples of focal parameters may be total daily basal amount and parameters regarding bolus doses (e.g., maximum doses and standard increments).

If processor 13 determines that the configuration file with one or more modified parameters does not contain a focal modified parameter, method and/or workflow 100 proceeds to step 108. In that step, processor 13 displays the modified parameters of the configuration file on user interface 14. In some embodiments, user interface 14 may display only the modified parameter(s). However, in other embodiments, user interface 14 may display the entire configuration file with the one or more modified parameter(s) highlighted. Additionally in step 108, the display may prompt a user to confirm the modified parameters of the configuration file. In step 110, a user may then confirm the displayed modified parameters of the configuration file through user interface 14 of computing device 12. In step 112, processor 13 writes the configuration file to medical device 24.

Referring back to step 106, if processor 13 determines that the configuration file contains one or more modified parameters that are focal, method and/or workflow 100 proceeds to step 114. In that step, processor 13 displays the modified parameters of the configuration file on user interface 14. In some embodiments, user interface 14 may display only the modified parameter(s). However, in other embodiments, such as the illustrated embodiment, user interface 14 may display the entire configuration file with the one or more modified parameter(s) highlighted. Additionally in step 114, the display may prompt a user to confirm the modified parameters of the configuration file. In step 116, a user may then confirm the displayed modified parameters of the configuration file through user interface 14 of computing device 12.

Once a user confirms the displayed modified parameters of the configuration file, method and/or workflow 100 moves on to step 118. In that step, a focal modified parameter is displayed on user interface 14, along with a prompting to have a user manually re-enter the displayed focal parameter. A user may then manually re-enter the focal modified parameter through user interface 14 of computing device 12. In step 120, processor 13 may automatically determine whether the manual re-entry of the displayed focal modified parameter matches the displayed focal modified parameter. If the manual re-entry of the displayed focal modified parameter matches the displayed focal modified parameter, processor 13 designates the displayed focal parameter as valid. Conversely, if the manual re-entry of the displayed focal modified parameter does not match the displayed focal modified parameter, processor 13 may automatically prompt for another manual re-entry of the displayed focal modified parameter or a change to the configuration file. Moreover, if the configuration file includes more than one focal modified parameter, steps 118 and 120 may be repeated for each focal modified parameter. Once all of the focal modified parameters have be designated as valid, the method may move to step 122. In step 122, processor 13 writes the configuration file to medical device 24.

In addition, FIGS. 5-16 provide screenshots from user interface 14 of computing device 12 during the execution of a particular embodiment of method and/or workflow 100 that is specific to adjusting the bolus dose standard increment parameter of a configuration file for an insulin pump. In this specific embodiment, the only modified parameter of the configuration file is the bolus dose standard increment, and that parameter is defined as focal. Accordingly, steps 102, 104, 106 and 114-122 are performed for method and/or workflow 100 illustrated in FIG. 4.

Figure 5:
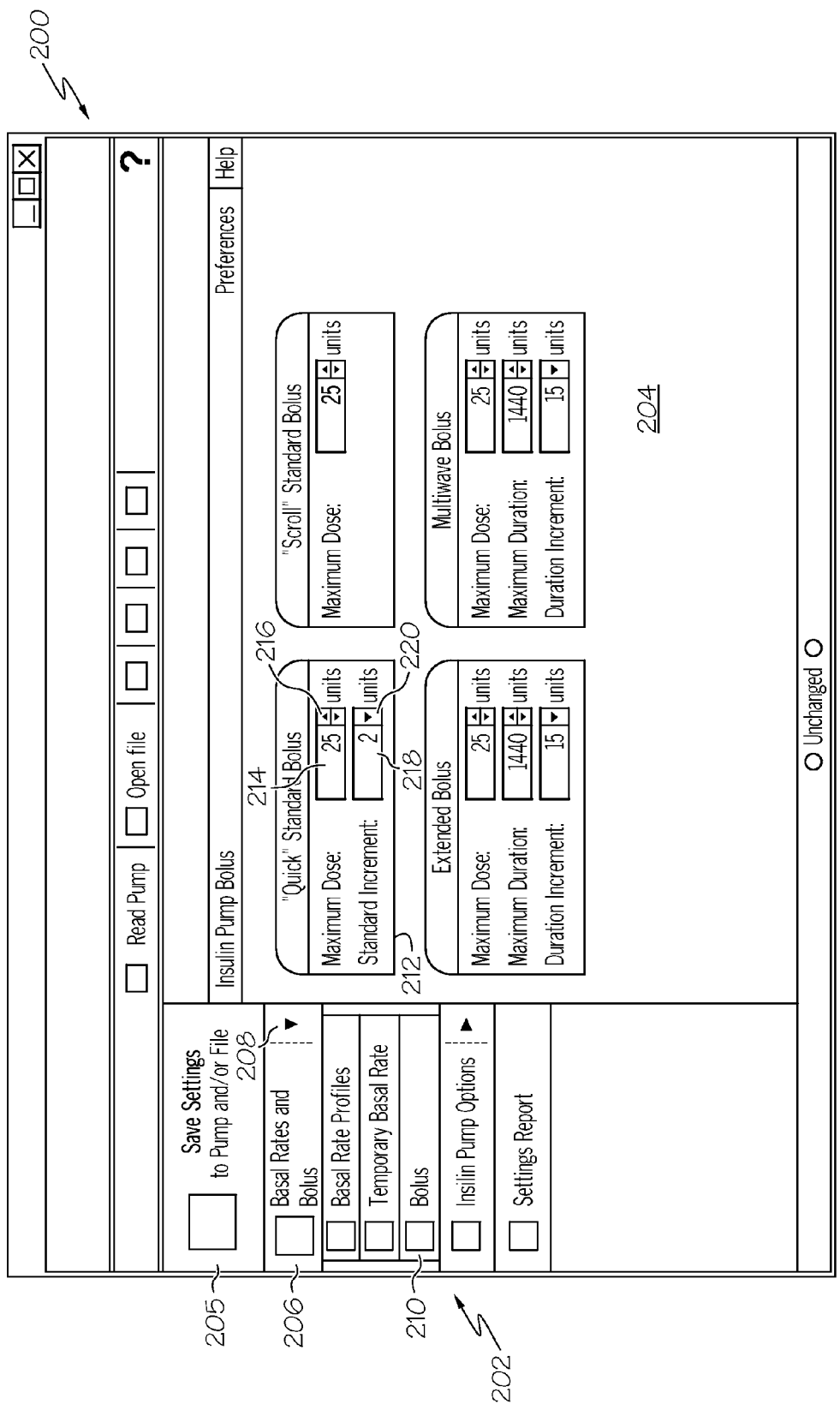
FIGS. 5-8 are screenshots relating to the modifying of a parameter of a configuration file.
Figure 6:
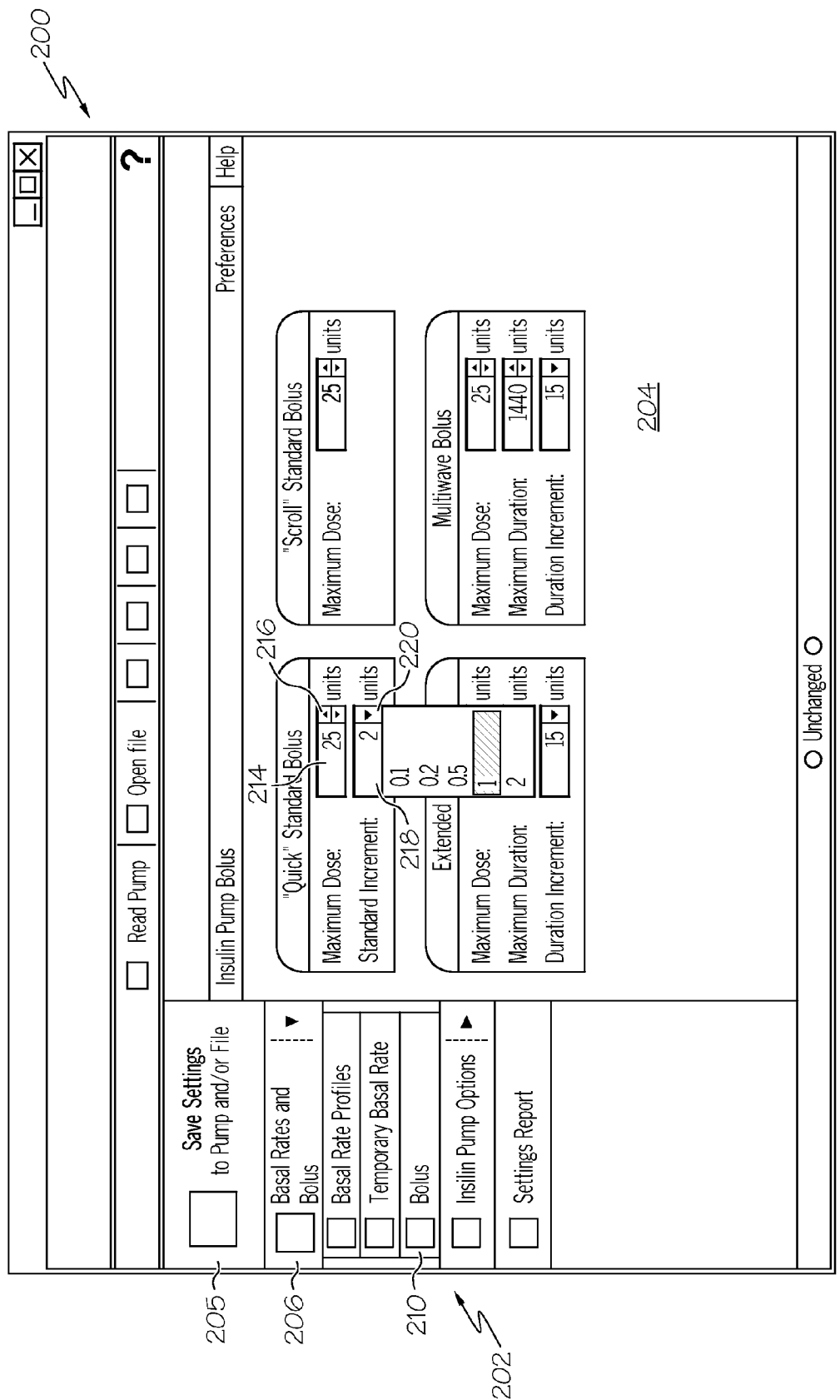
Figure 7:
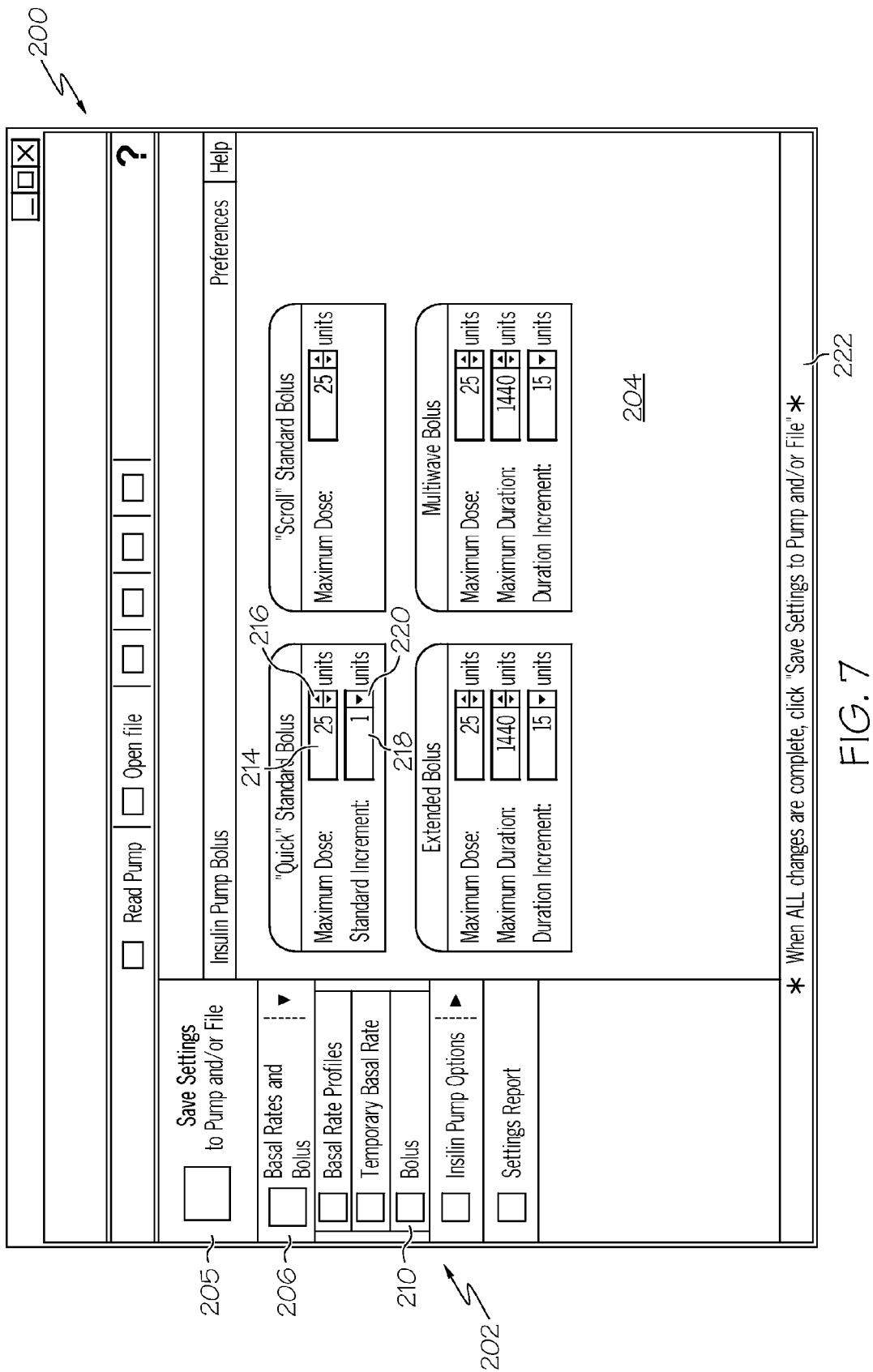

FIG. 5 depicts a parameter modification screen 200 of user interface 14 that is displayed when a user utilizes computing device 12 to modify the parameters of a configuration file. Screen 200 generally includes a navigation menu 202 and an active window 204. Navigation menu 202 includes a Save Settings button 205 and a Basal Rates and Bolus button 206 with an indicator 208 denoting the existence of a dropdown menu associated with button 206. The content displayed in active window 204 changes depending on the operation being performed by software 17 (which contains and/or has access to a computer readable medium tangibly embodying method and/or workflow 100). In the screenshot of FIG. 5, indicator 208 has been activated, and three sub-options under button 206 have been presented. Of those presented options, a Bolus button 210 has been activated. Accordingly, the activation of button 210 requires software 17 to control active window 204 to display four boxes relating to the modification of bolus parameters. One of those four boxes is "Quick" Standard Bolus box 212. Box 212 includes a Maximum Dose data entry box 214 with an indicator 216 denoting the existence of a dropdown menu associated with button 214, and a Standard Increment data entry box 218 with an indicator 220 denoting the existence of a dropdown menu associated with button 218. As shown in FIG. 6, when indicator 220 is activated, five sub-options under data entry box 218 are presented. The sub-option of 1 has been highlighted for selection. In FIG. 7, the sub-option for 1 has been selected, and is displayed in data entry box 218. The message 222 displayed along the bottom of the screenshot in FIG. 7 indicates at least one parameter of the configuration file has been modified.

Figure 8:
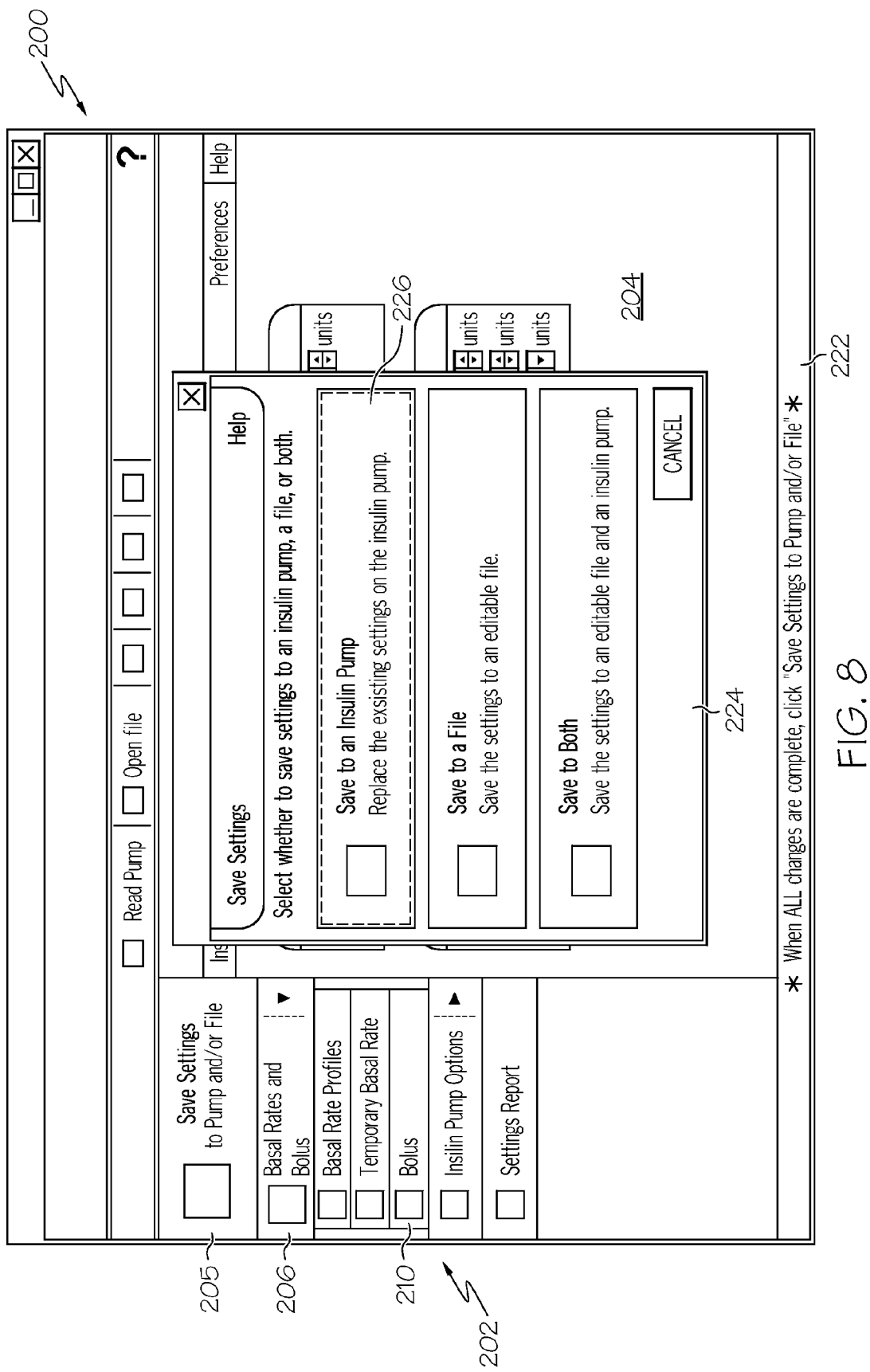
Figure 9:
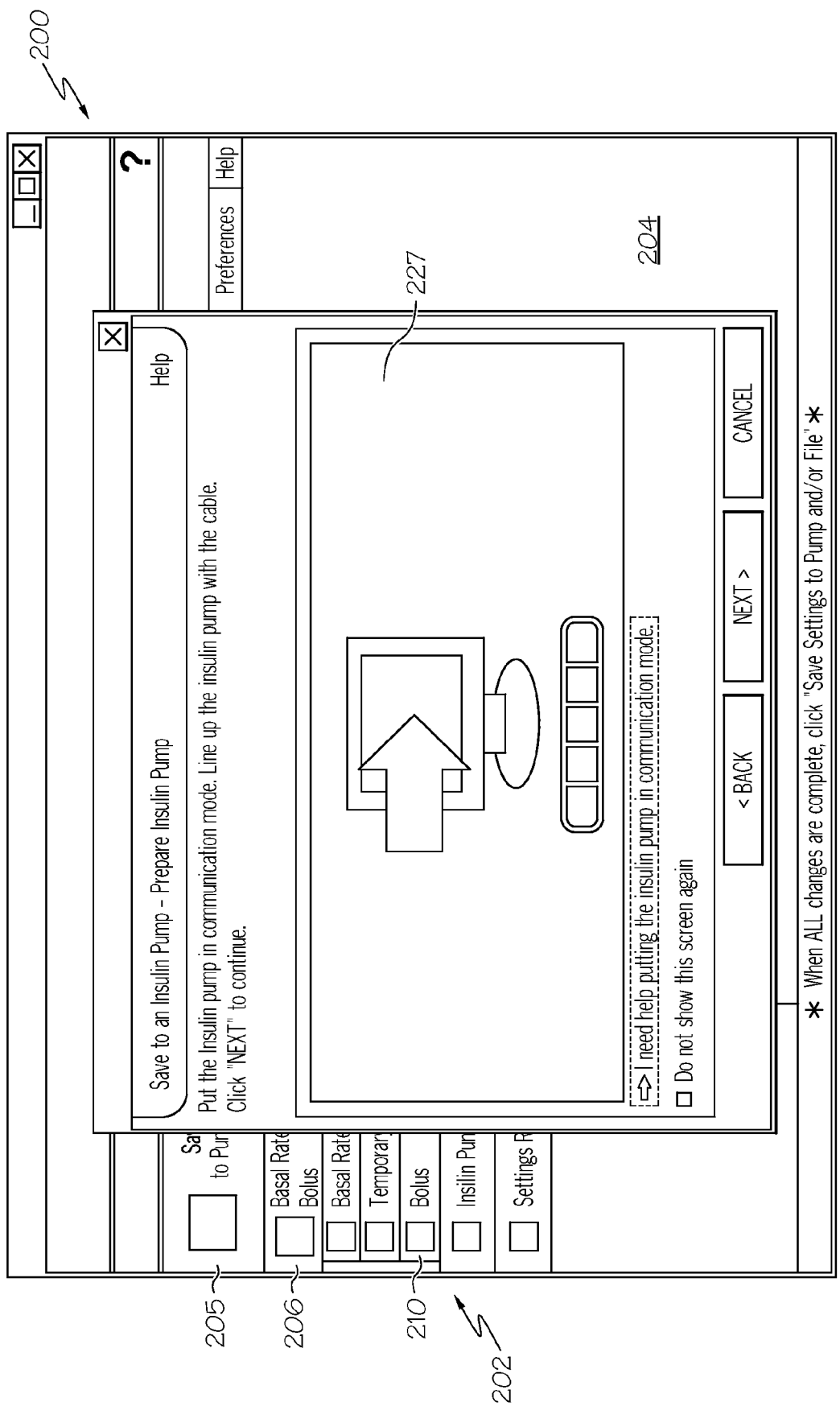
FIGS. 9-11 are screenshots relating to the establishing of communication between a medical device and a computing device.
Figure 10:
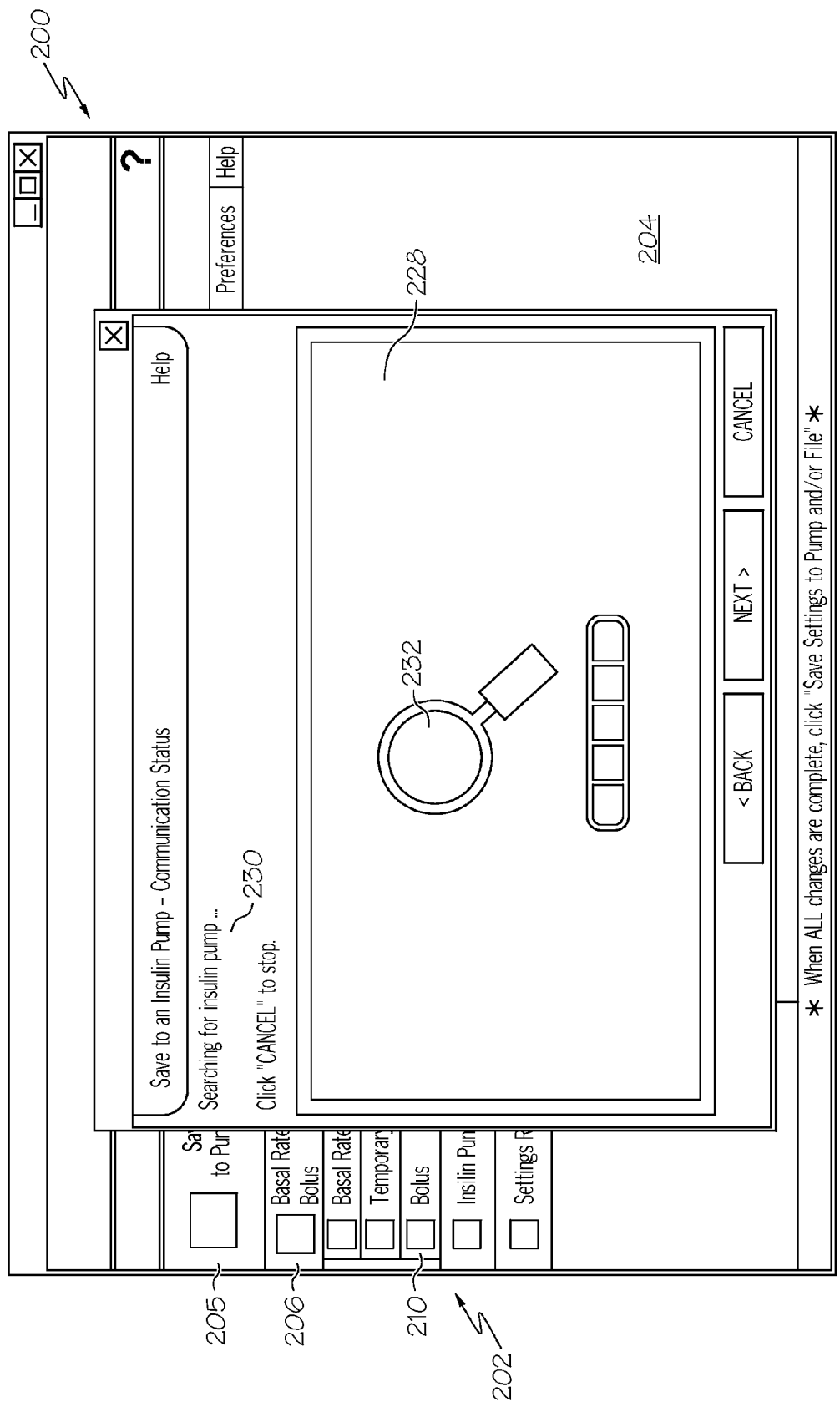
Figure 11:
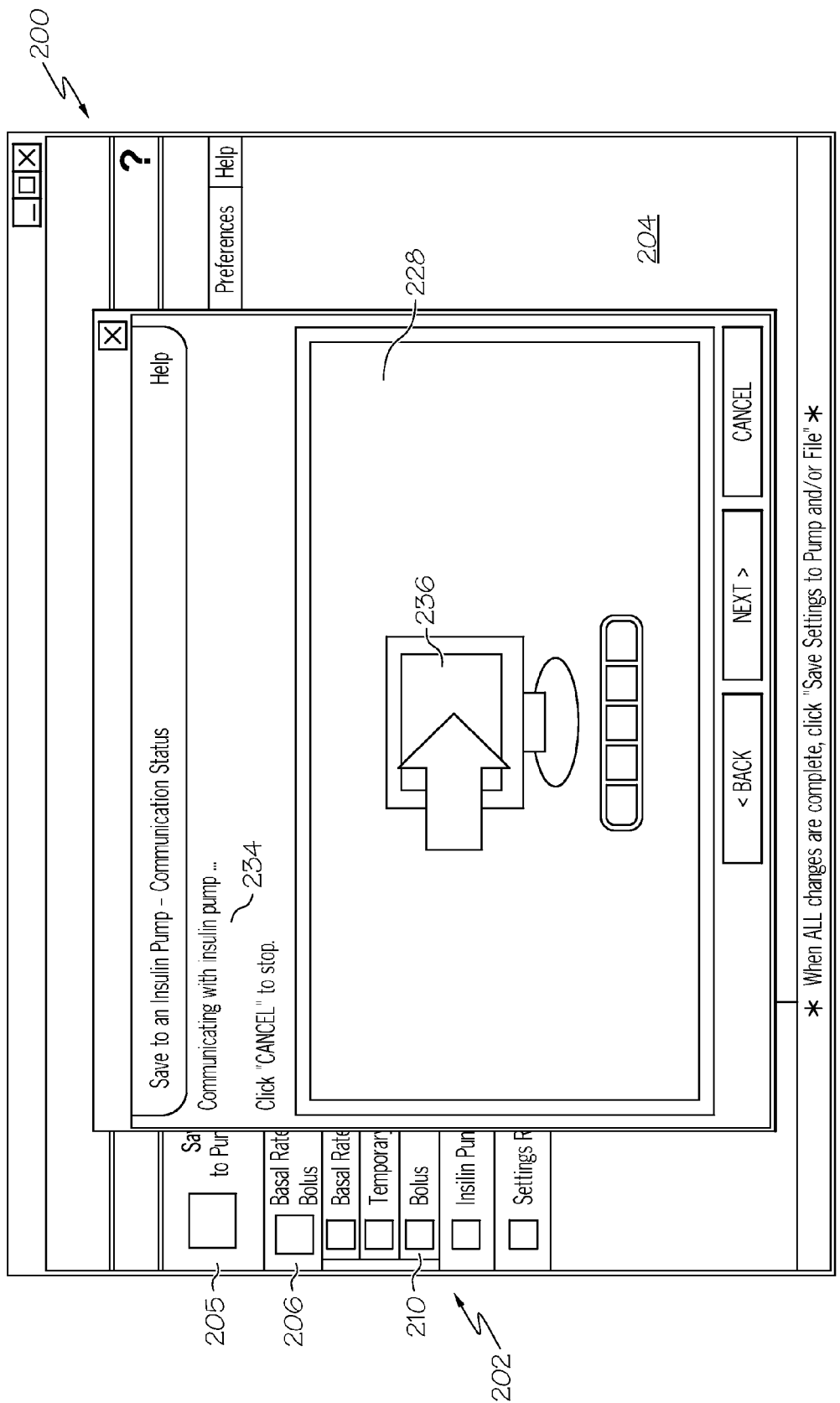

The screenshot of FIG. 8 illustrates that button 205 has been activated, causing software 17 to control a pop-up Save Settings dialog box 224 to be displayed over active window 204. On dialog box 224, the Save to an Insulin Pump button 226 has been selected. As illustrated in FIG. 9, after button 226 is activated, software 17 controls a pop-up Save to an Insulin Pump—Prepare Insulin Pump dialog box 227 to be displayed over active window 204. At this point, a user would line up medical device 24 with dongle 26 connected to computing device 12 to establish communication between the medical device and the computing device. The screenshot of FIG. 10 illustrates a Save to an Insulin Pump—Communication Status dialog box 228 displayed over active window 204, in which a message "Searching for insulin pump . . . " 230 and a magnifying glass icon 232 are displayed. At this point, computing device 12 is attempting to establish communication with medical device 24. As illustrated in the screenshot of FIG. 11, once communication is established, the message of dialog box 228 changes to "Communicating with insulin pump . . . " 234 and the icon changes to a computer/arrow icon 236. At this point, communication between the computing device 12 and medical device 24 has been established.

Figure 12:
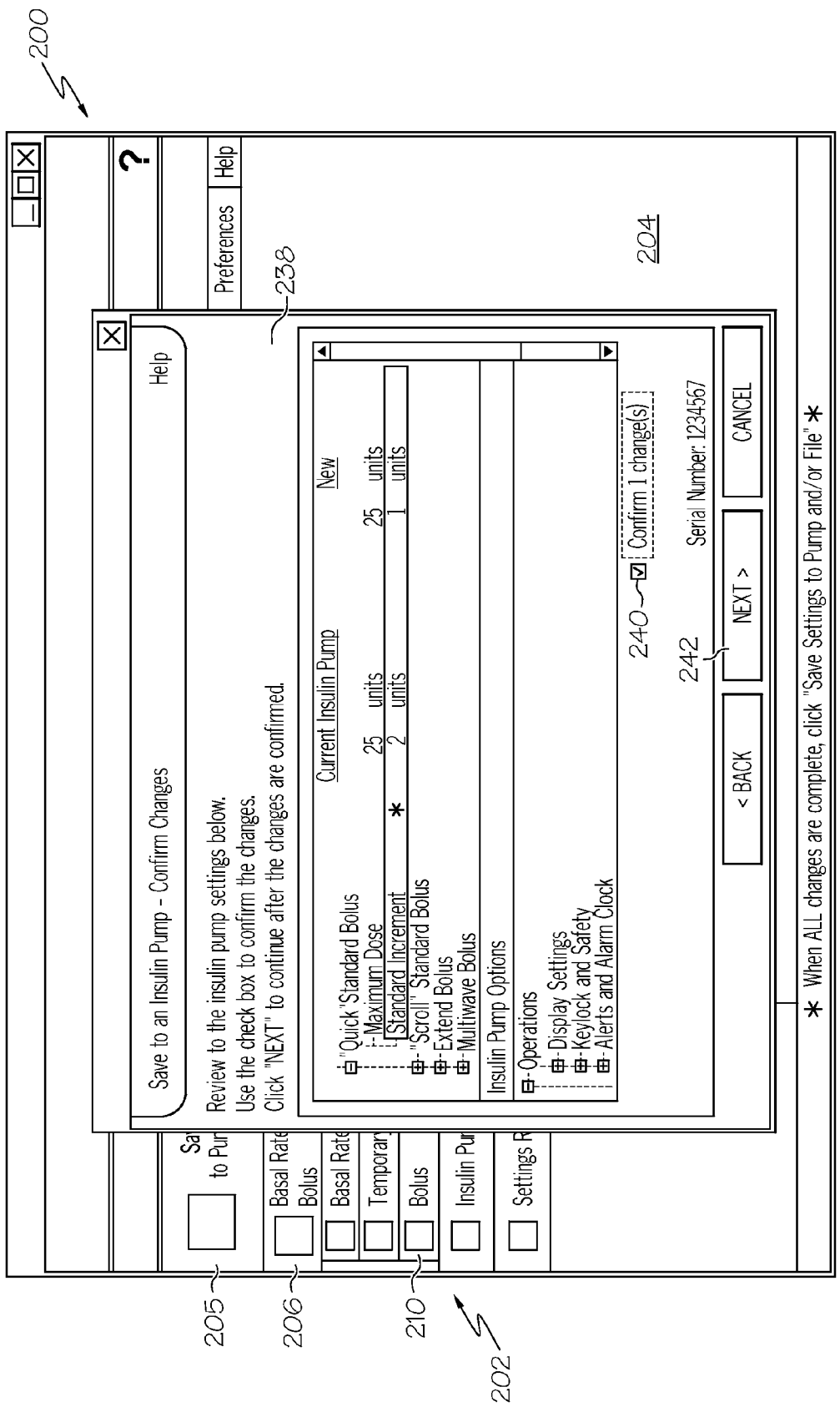
FIG. 12 is a screenshot relating to the displaying of a modified parameter of a configuration file and the prompting of a confirmation of the modified parameter.
Figure 13:
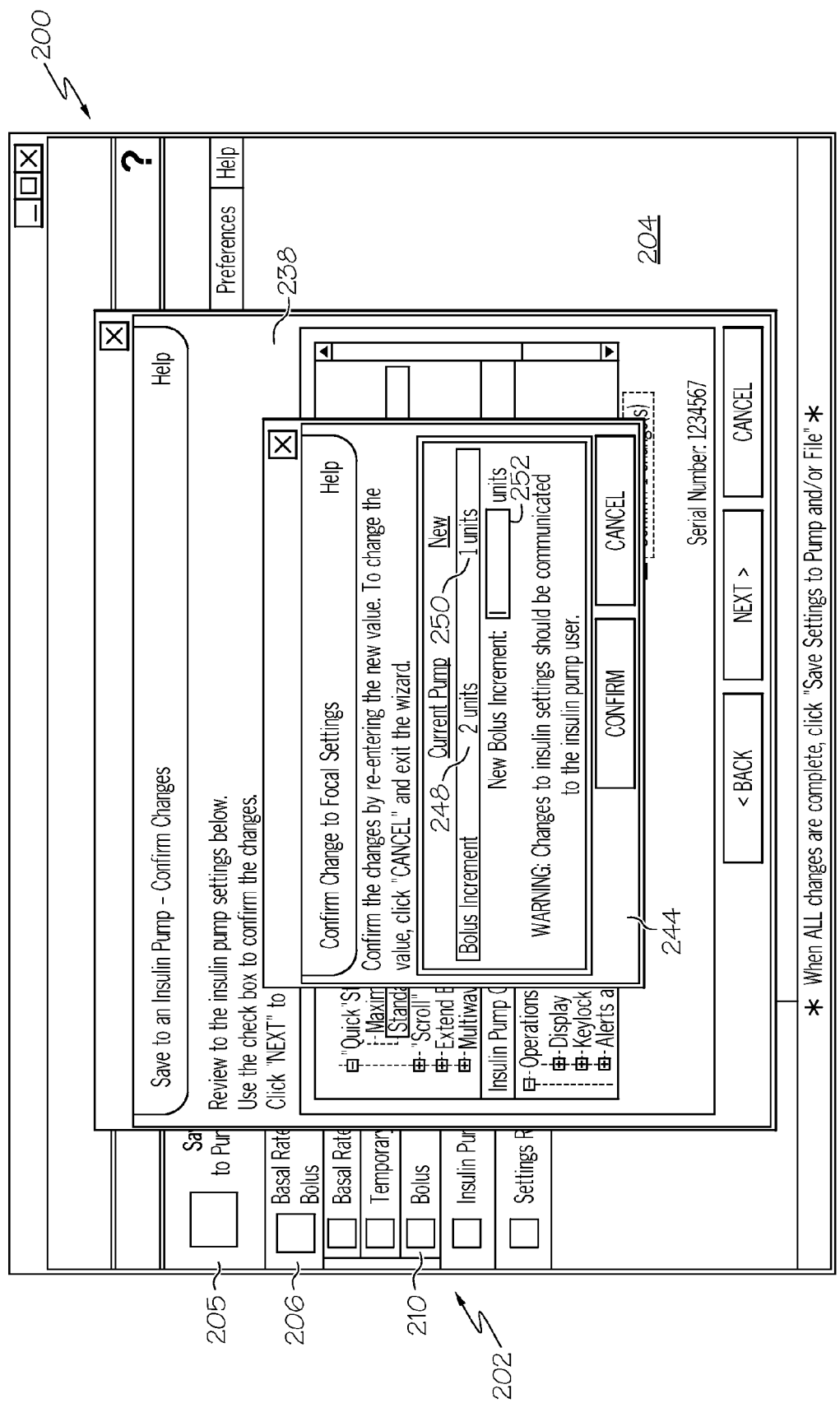
FIG. 13 is a screenshot relating to the displaying of a determined focal parameter and the prompting of a manual re-entry of the displayed focal modified parameter.
Figure 14:
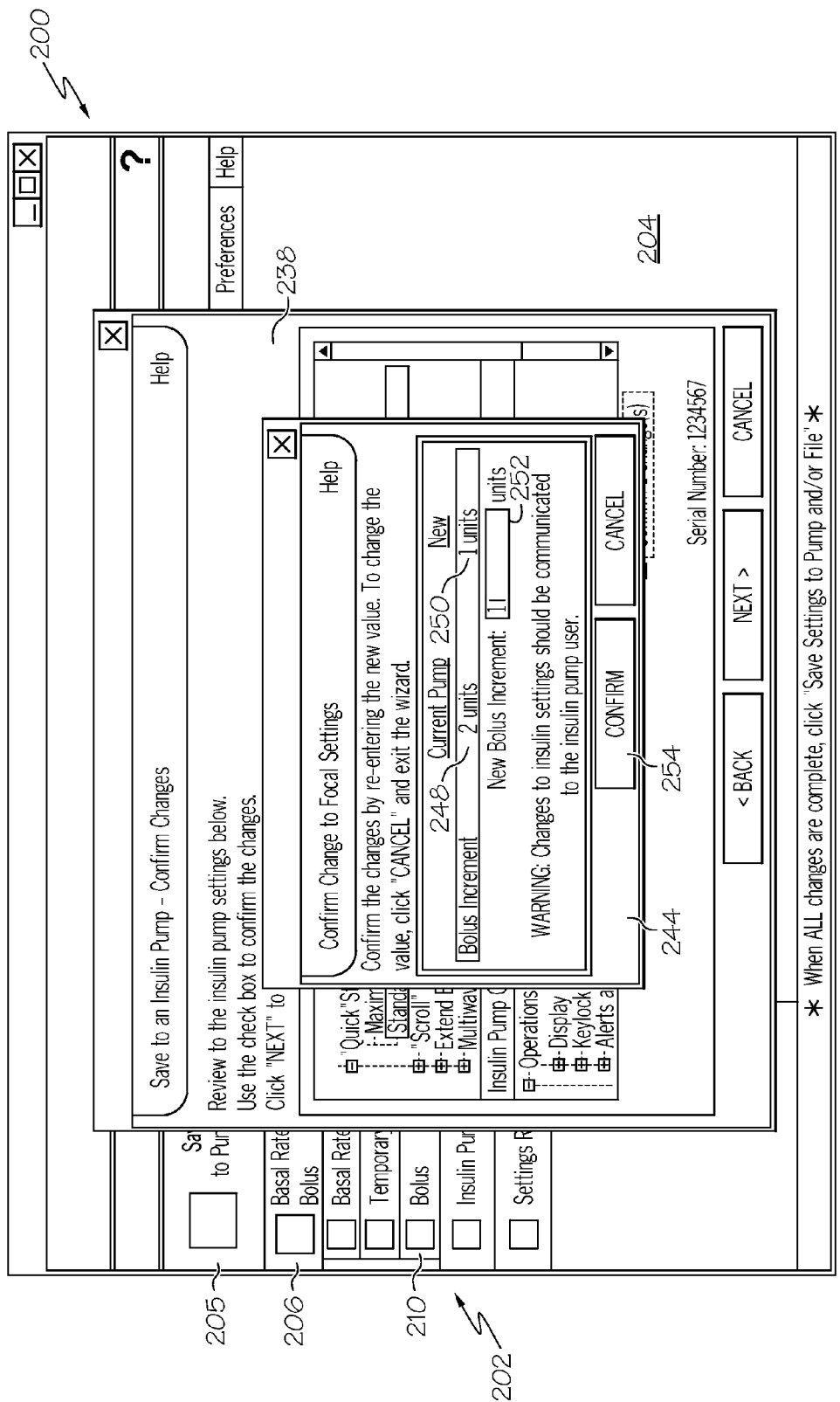
FIG. 14 is a screenshot relating to the receiving of a manual re-entry of the displayed focal modified parameter.

Once communication is established, processor 13 automatically reads the modified parameter of the configuration file ("Quick" Standard Bolus—Standard Increment parameter changed from 2 units to 1 unit), and makes the determination that the modified parameter is focal (because such a modification was previously defined as focal). Accordingly, referring to FIG. 4, the method and/or workflow goes from step 106 to step 114. As illustrated in the screenshot of FIG. 12, software 17 controls a Save to an Insulin Pump—Confirm Changes dialog box 238 to be displayed over active window 204. The one modified parameter of the configuration file ("Quick" Standard Bolus, Standard Increment) is displayed in dialog box 238 with the modification highlighted. At this point, if a user agrees with the parameter modification, a user then checks box 240 for "Confirm 1 Change(s)" and activates the NEXT button 242. When NEXT button 242 is activated, as illustrated in FIG. 13, processor 13 automatically displays a Confirm Change to Focal Setting dialog box 244 over dialog box 238, which is displayed over active window 204. Dialog box 244 includes identification of the particular focal parameter being modified, the current parameter setting 248 and the modified parameter setting 250. Dialog box 244 also includes a data entry window 252 for manually re-entering the focal modified parameter. At this time, a user would utilize user interface 14 of computing device 12 to re-enter the focal modified parameter. The screenshot of FIG. 14 illustrates the focal modified parameter manually re-entered into data entry window 252. Once the modified parameter has been manually re-entered, the CONFIRM button 254 is activated.

Figure 15:
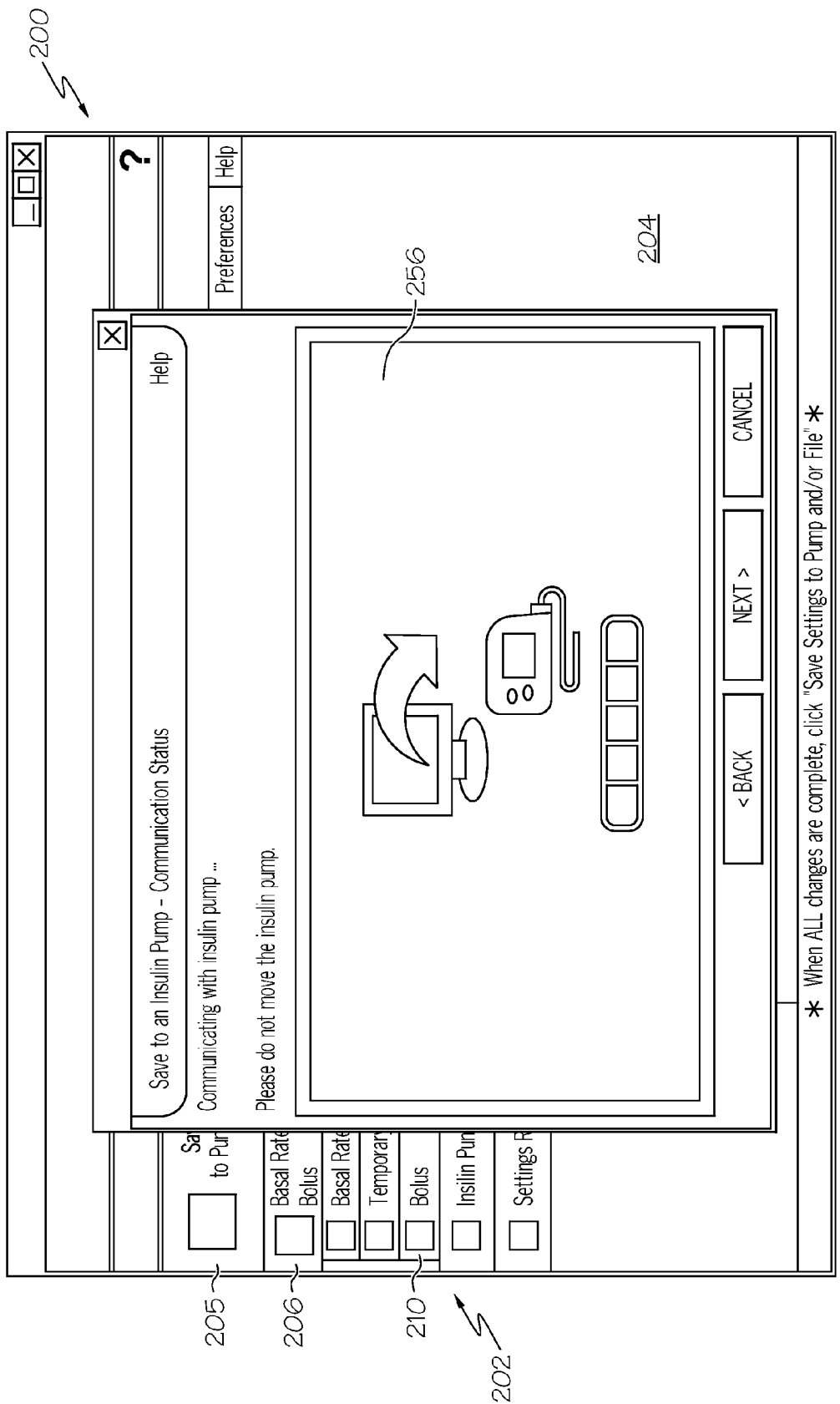
FIGS. 15-16 are screenshots relating to the writing of a configuration file to a medical device.
Figure 16:
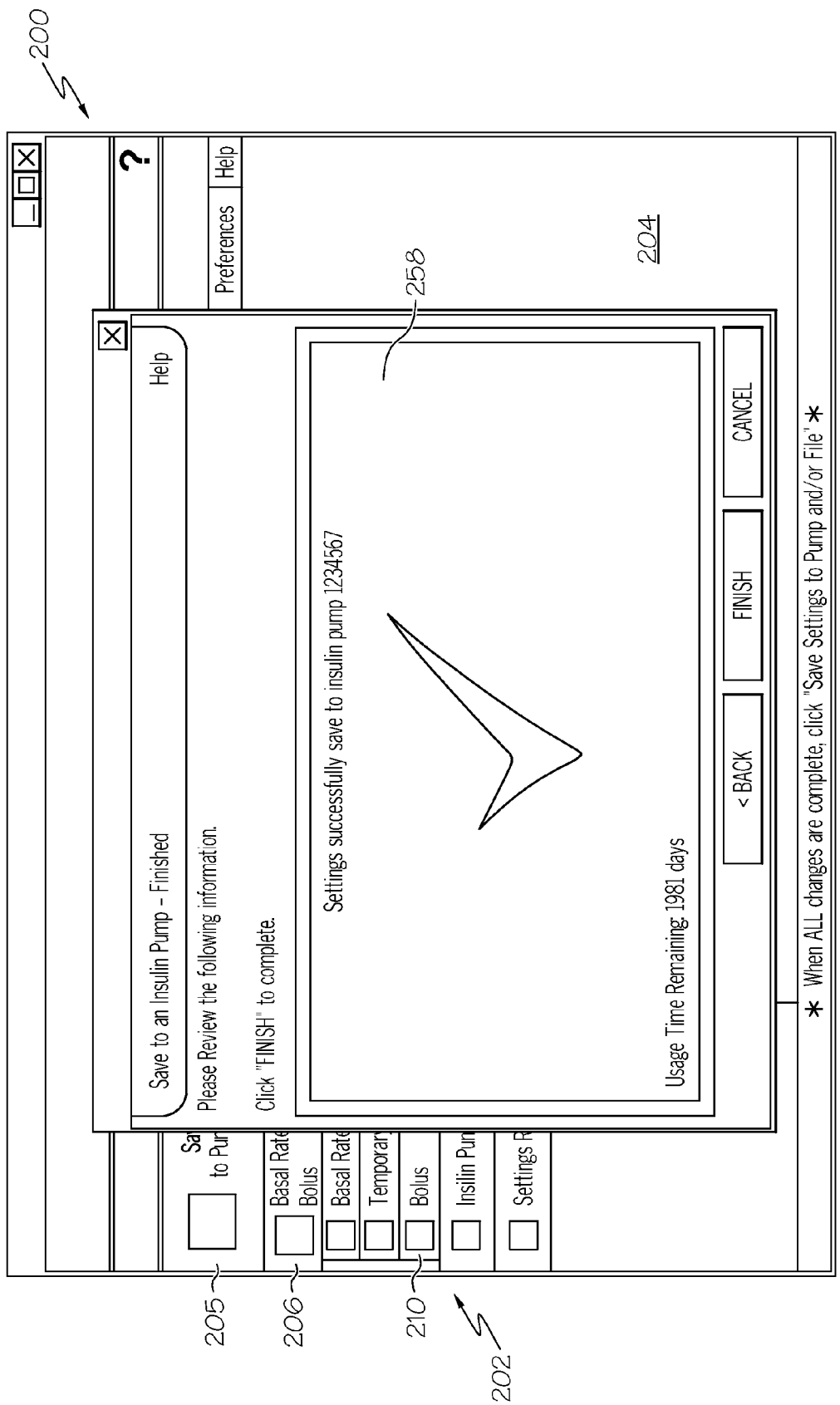

With the focal modified parameter manually re-entered, processor 13 automatically determines if the re-entry of the displayed focal modified parameter matches the displayed focal modified parameter. The two values match, and processor 13 designates the displayed focal parameter as valid. If the configuration file contained more than one focal modified parameter, the screenshots/steps of FIGS. 13 and 14 would be repeated for each additional focal modified parameter. However, because the configuration file only contained one focal modified parameter, every focal modified parameter has been designated valid. Accordingly, processor 13 automatically controls computing device 12 to communicate with medical device 24 in order to write the configuration file to the medical device. This process is illustrated in FIG. 15, wherein the Save to an Insulin Pump—Communication Status dialog box 256 is shown. As illustrated in FIG. 16, when the new configuration file is written to medical device 24, the Save to an Insulin Pump—Finished dialog box 258 is displayed.

While an exemplary embodiment incorporating the principles of the present teachings has been disclosed hereinabove, the present teachings are not limited to the disclosed embodiments. Accordingly, this application is intended to cover any variations, uses or adaptations of the disclosed general principles. Further, this application is intended to cover such departures from the present disclosure as come within known or customary practice in the art to which this application pertains and which fall within the limits of the appended claims.

What is claimed is:

1. An error-reducing method for operating a computing device that includes a user interface, a processor and memory to configure a medical device, the method being performed by the processor and comprising:

displaying on the user interface a parameter modification screen having a navigation menu and an active window that a user utilizes to modify parameters of a configuration file of the medical device, wherein content displayed in active window changes depending on the operation being performed;

receiving manual input via the user interface from the user which modifies one or more parameters in the configuration file resulting in one or more modified parameters;

receiving manual input via the user interface from the user of a saving selection;

establishing communication with the medical device in response to the saving selection being to the medical device;

determining automatically if the one or more modified parameter in the configuration file is focal in that the one or more modified parameter are unique to the patient and remaining ones of the modified parameters are non-focal in that the remaining ones of the modified parameters are suitable for any patient of the medical device;

displaying the entire configuration file with the modified parameters highlighted on the display screen in response to determining that the configuration file contains modified parameters that are focal;

displaying only the modified parameters if the processor determines that the configuration file does not contain the modified parameters that are focal;

prompting a manual confirmation for each of the displayed and highlighted modified parameters;

receiving the manual confirmation through the user interface from the user for each of the displayed and highlighted modified parameters;

prompting automatically for a manual re-entry of the modification to a displayed and highlighted modified parameter which is focal in response to receiving the manual confirmation;

receiving through the user interface the manual re-entry of the modification to the displayed and highlighted focal modified parameter that is focal;

determining automatically whether the manual re-entry of the modification to the displayed and highlighted focal modified parameter matches the displayed and highlighted focal modified parameter;

designating the displayed and highlighted focal modified parameters as valid if the manual re-entry of the modification to the displayed and highlighted focal modified parameter matches the displayed and highlighted focal modified parameter, otherwise prompting for another manual re-entry of the displayed and highlighted focal modified parameter or a change to the configuration file;

storing automatically the configuration file in memory of the medical device once every determined focal modified parameter has been designated valid; and wherein the navigation menu includes a Save Settings button and a Basal Rates and Bolus button with an indicator denoting the existence of a dropdown menu.

2. The method of claim 1, wherein the content in one operation relates to the modification of bolus parameters.

3. The method of claim 1, wherein the content in one operation related to the modification of bolus parameters that include Standard Bolus box having a Maximum Dose data entry box, and a Standard Increment data entry box.

4. The method of claim 1, wherein a message is displayed along the bottom of the screen to indicate at least one parameter of the configuration file has been modified.

5. The method of claim 1, further comprising displaying a dialog box on the user interface to designate the saving selection of saving the configuration file containing the one or more modified parameters to memory or to the medical device.

6. The method of claim 1, wherein the medical device comprises an insulin pump.

7. The method of claim 1, wherein the focal modified parameters are selected from a group comprising total daily basal amount and bolus dose.

8. The method of claim 1, wherein the computing device is disposed on or within an insulin pump or a glucose meter.

9. The method of claim 1, wherein the computing device is selected from a group comprising a computer, a medical website, a stand-alone device, a hub device and a pass-through device.

10. A computing device for configuring a medical device of a patient comprising:
  a user interface;
  memory; and
  a processor connected to the user interface, and the memory, the processor configured to:
  display on the user interface a parameter modification screen having a navigation menu and an active window that a user utilizes to modify parameters of a configuration file of the medical device, wherein content displayed in active window changes depending on the operation being performed,
  receive manual input via the user interface from the user which modifies one or more parameters in the configuration file resulting in one or more modified parameters,
  receive manual input via the user interface from the user of a saving selection,
  establish communication with the medical device in response to the saving selection being to the medical device,
  determine automatically if the one or more modified parameter in the configuration file is focal in that the one or more modified parameter are unique to the patient and remaining ones of the modified parameters are non-focal in that the remaining ones of the modified parameters are suitable for any patient of the medical device,
  display the entire configuration file with the modified parameters highlighted on the display screen in response to determining that the configuration file contains modified parameters that are focal,
  display only the modified parameters if the processor determines that the configuration file does not contain the modified parameters that are focal;
  prompt a manual confirmation for each of the displayed and highlighted modified parameters,
  receive the manual confirmation through the user interface from the user for each of the displayed and highlighted modified parameters,
  prompt automatically for a manual re-entry of the modification to a displayed and highlighted modified parameter which is focal in response to receiving the manual confirmation,
  receive through the user interface the manual re-entry of the modification to the displayed and highlighted focal modified parameter that is focal,
  determine automatically whether the manual re-entry of the modification to the displayed and highlighted focal modified parameter matches the displayed and highlighted focal modified parameter,
  designate the displayed and highlighted focal modified parameters as valid if the manual re-entry of the modification to the displayed and highlighted focal modified parameter matches the displayed and highlighted focal modified parameter, otherwise prompting for another manual re-entry of the displayed and highlighted focal modified parameter or a change to the configuration file,
  store automatically the configuration file in memory of the medical device once every determined focal modified parameter has been designated valid; and
  wherein the navigation menu includes a Save Settings button and a Basal Rates and Bolus button with an indicator denoting the existence of a dropdown menu.

11. The computing device of claim 10, wherein the modified parameters are focal if the modified parameters relate to insulin dosage rates which include any of the modified parameter to the hourly basal rates, the maximum hourly basal rates, the maximum daily basal rates, and the bolus dose settings and the modified parameters are not focal if the modified parameters relate to the communication settings, the battery settings, and the language setting.

12. The computing device of claim 10, wherein the computing device is configured to establish communications with an insulin pump and automatically read the configuration file from memory of the insulin pump.

13. The computing device of claim 10, wherein the medical device is an insulin pump.

14. The computing device of claim 10, wherein the computing device is selected from a group comprising a glucose meter, a computer, a medical website, a stand-alone device, a hub device and a pass-through device.

15. The computing device of claim 10, wherein the computing device is disposed on or within a glucose meter or an insulin pump.

16. The computing device of claim 10, wherein the content in one operation related to the modification of bolus parameters that include Standard Bolus box having a Maximum Dose data entry box, and a Standard Increment data entry box.

17. The computing device of claim 10, wherein a message is displayed along the bottom of the screen by the processor to indicate at least one parameter of the configuration file has been modified.

18. The computing device of claim 10, wherein the processor is configured to display a dialog box on the user interface to designate the saving selection of saving the configuration file containing the one or more modified parameters to memory or to the medical device.

* * * * *